United States Patent
Huebner

[11] Patent Number: 5,868,789
[45] Date of Patent: *Feb. 9, 1999

[54] REMOVABLE SUTURE ANCHOR APPARATUS

[76] Inventor: Randall J. Huebner, 18650 S. W. Hart Rd., Aloha, Oreg. 97005

[*] Notice: This patent issued on a continued prosecution application filed under 37 CFR 1.53(d), and is subject to the twenty year patent term provisions of 35 U.S.C. 154(a)(2).

[21] Appl. No.: 792,988

[22] Filed: Feb. 3, 1997

[51] Int. Cl.$^6$ .................................................. A61B 17/50
[52] U.S. Cl. ........................................... 606/232; 606/73
[58] Field of Search ............................... 606/232, 60, 72, 606/73, 75, 104, 148

[56] References Cited

U.S. PATENT DOCUMENTS

| | | |
|---|---|---|
| D. 331,463 | 12/1992 | Rosenberg et al. . |
| D. 374,287 | 10/1996 | Goble et al. . |
| D. 374,482 | 10/1996 | Goble et al. . |
| 4,632,100 | 12/1986 | Somers et al. . |
| 4,898,156 | 2/1990 | Gatturna et al. . |
| 4,899,743 | 2/1990 | Nicholson et al. . |
| 4,946,468 | 8/1990 | Li . |
| 5,037,422 | 8/1991 | Hayhurst et al. . |
| 5,041,129 | 8/1991 | Hayhurst et al. . |
| 5,064,425 | 11/1991 | Branemark et al. ........................ 606/72 |
| 5,100,417 | 3/1992 | Cerier et al. . |
| 5,120,171 | 6/1992 | Lasner ....................................... 411/308 |
| 5,122,132 | 6/1992 | Bremer ....................................... 606/72 |
| 5,141,520 | 8/1992 | Goble et al. . |
| 5,156,616 | 10/1992 | Meadows et al. . |
| 5,246,441 | 9/1993 | Ross et al. ................................. 606/53 |
| 5,258,016 | 11/1993 | DiPoto et al. ............................ 606/232 |
| 5,354,298 | 10/1994 | Lee et al. ................................... 606/72 |
| 5,364,400 | 11/1994 | Rego, Jr. et al. ........................ 606/72 |
| 5,370,662 | 12/1994 | Stone et al. . |
| 5,443,482 | 8/1995 | Stone et al. . |
| 5,562,672 | 10/1996 | Huebner et al. ............................ 606/73 |
| 5,573,548 | 11/1996 | Nazre et al. .............................. 606/232 |
| 5,607,432 | 3/1997 | Fucci ....................................... 606/104 |
| 5,618,314 | 4/1997 | Harwin et al. ............................ 606/232 |
| 5,643,320 | 7/1997 | Lower et al. .............................. 606/232 |
| 5,683,401 | 11/1997 | Schmieding et al. .................... 606/104 |
| 5,683,418 | 11/1997 | Luscombe et al. ....................... 606/232 |
| 5,720,766 | 2/1998 | Zang et al. ............................... 606/232 |

OTHER PUBLICATIONS

"Surgical Technique" and Easy, Revisionary, Strong information pages from Ogden Anchor re AME Ogden anchors.

"The Anchor That Holds Fast" information page from Linvatec re one–step suture anchor.

"Mitek GII Snap" information pages from Mitek Surgical Products, Inc. re GH anchors.

"Rotator Cuff Repair With a New Twist" information page from Linvatec Corporation re Revo cancellous screw.

*Primary Examiner*—Michael Buiz
*Assistant Examiner*—Tina T. D. Pham
*Attorney, Agent, or Firm*—Kolisch, Hartwell, Dickinson, McCormack & Heuser

[57] ABSTRACT

A suture anchor apparatus for anchoring a suture in a bone. The apparatus includes an anchor with an elongate tip, a threaded portion and a suture securing structure coupled to the threaded portion. The tip includes a leading end, a trailing end and a longitudinal axis extending therebetween. The tip further has a length measured from the leading end to the trailing end, a width measured at the trailing end and an aspect ratio equal to the length divided by the width. The threaded portion is coupled to the trailing end of the tip and extends back therefrom and includes a generally cylindrical root with a screw thread formed thereon. The root has an elongate axis collinear with the longitudinal axis of the tip and the threads having an outside diameter substantially greater than the width of the tip. The aspect ratio and length of the tip are configured to make the anchor stable with only the tip inserted into the bone.

25 Claims, 4 Drawing Sheets

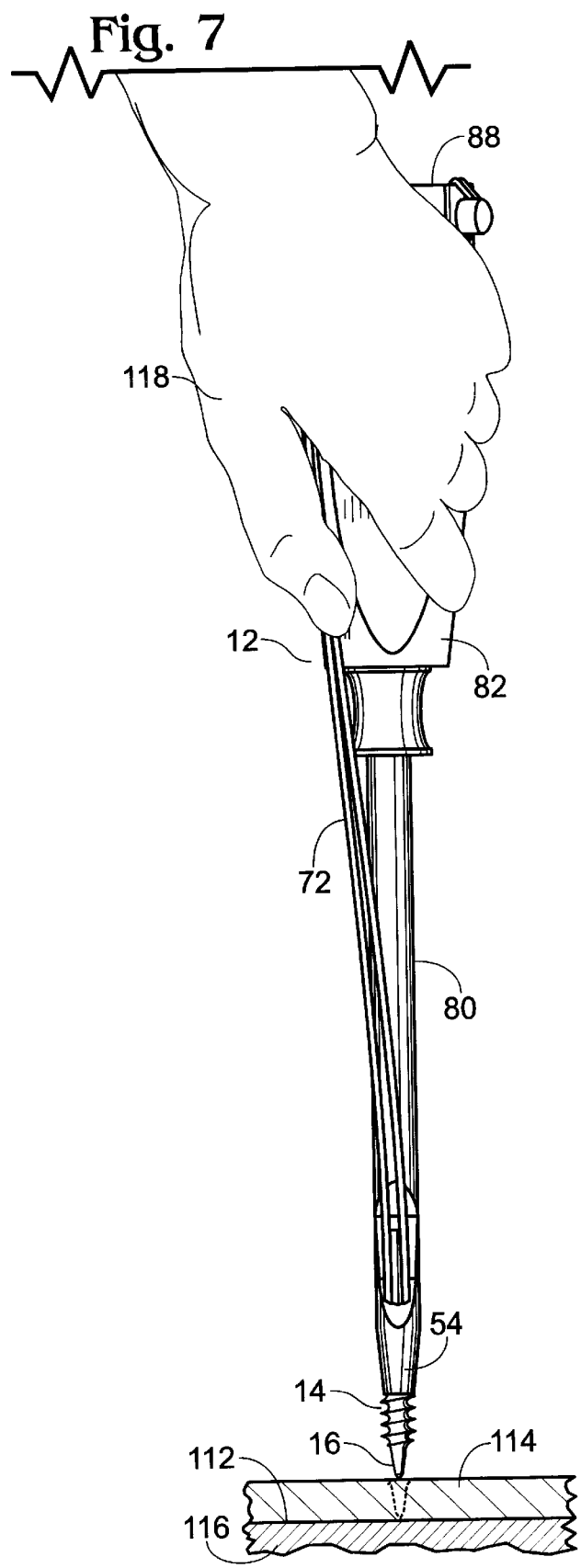
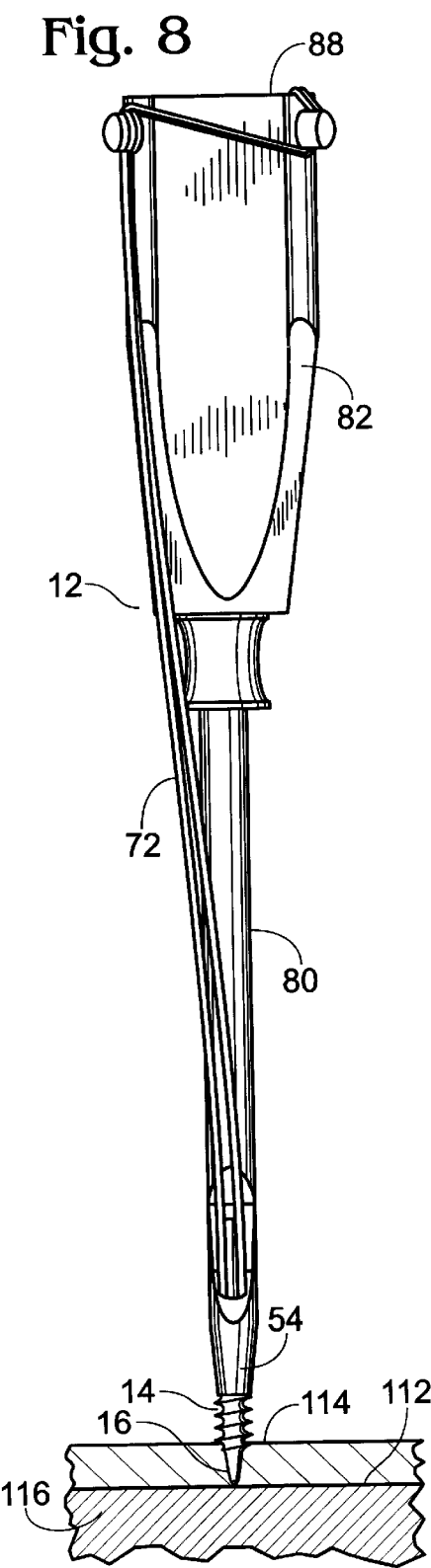

REMOVABLE SUTURE ANCHOR APPARATUS

FIELD OF THE INVENTION

The present invention relates generally to a device for use in orthopedic surgical procedures for anchoring suture to bone. More specifically, it concerns a suture anchor and a driver used to insert the anchor in a bone and also remove the anchor from the bone.

BACKGROUND

Suture anchors are used in orthopedic surgery to, for example, reattach a ligament to a bone after the ligament has been separated from the bone by a sports injury. Suture anchors are inserted into the bone and include barbs, threads or other means to resist pullout force applied to the anchor. Anchors typically include an eyelet or other structure to secure a length of suture. The suture is used to draw a ligament against the bone. With the ligament held to the bone, preferably at or near the original attachment point, the ligament is able to reattach to the bone. Suture anchors are normally made of either a bio-absorbable compound or a bio-compatible material because the anchor is often covered by the reattached ligament once the healing process is completed and cannot be easily removed.

Suture anchors can be either removable or non-removable after initial placement. Non-removable suture anchors are typically hammered or pushed into the bone, either with or without a pre-drilled hole, and retained by barbs that resist pullout. Removable suture anchors are typically threaded and may be screwed into the bone for anchoring and unscrewed from the bone for removal. Some removable suture anchors include a hole-starting drill bit that bores a hole in the bone ahead of the threaded portion. This eliminates the need to pre-drill a pilot hole for the anchor. One drawback of such an anchor is that, as the drill bit bores through the bone, it may migrate and the path of the hole may be widened or misdirected from the originally intended location. It is therefore difficult to accurately place self-drilling anchors.

A suture anchor is best placed as close as possible to the original attachment point of the ligament to facilitate reattachment. However, with existing anchors, this is often difficult due to interference from surrounding soft tissue or bones. The first site chosen for an anchor may be determined to be unsuitable for various reasons that may not be known until after insertion. For instance, the underlying bone structure may be incapable of supporting the anchor properly. The anchor must then be re-sited in a different location. Re-siting is impossible with non-removable anchors, multiple anchors must be implanted instead.

Removable anchors make re-siting possible but existing removable anchors have several drawbacks. Existing removable anchors create a hole, either pre-drilled or drilled by the anchor, with a diameter and a depth corresponding to the size of the anchor. The hole is generally cylindrical in shape, but may be irregular and even larger than the root portion of the anchor if the drill was not maintained at a constant angle throughout the drilling process. As a result, the bone structure is weakened around the drilled hole. If the anchor must be re-sited, the surgeon must avoid the area around the previous hole, sometimes resulting in a placement that is less than surgically optimal.

With known removable anchors, the area within a diameter of the original hole is generally precluded from re-siting for several reasons. First, there is the likelihood that a hole drilled close to the original hole would migrate into the original hole resulting in further bone structure damage and another unusable hole. Second, the re-sited hole must not overlap the original hole or the threads in the overlapping area would have no bone purchase. Third, the re-sited hole must be moved a certain distance from the first hole, around which the bone structure has been weakened, to an area where the bone structure has not been weakened so that the full pullout strength is available to secure the ligament tightly to the bone.

Preferably, an anchor should be quickly, easily and removably insertable to an assessment position while producing the minimum impact on bone structure. When re-siting is necessary, the damage to the bone at the original site should not significantly impact the surgeon's choice for a second site. Furthermore, the anchor should be predictably insertable along a path to a precise final position.

Existing drivers for removable suture anchors also suffer from a number of deficits. In particular, some drivers utilize a small hex drive to couple to the anchor, and such drives are subject to stripping wherein the comers of the hex are rounded off. The surgeon must then grab the anchor with pliers or a similar device and attempt to remove it. Existing drivers are also sometimes difficult to load with the suture. With drivers that are cannulated to pass the suture, a special tool is often required to insert the suture through the driver. This arrangement can make use of a suture with a pre-attached needle difficult or impossible. In the case of drivers where the suture extends laterally rather than up through the driver, the suture can become tangled with the driver as the anchor is driven in. In either case, the needle remains exposed during installation of the suture, with the accompanying risk of an accidental needle stick. It is therefore an object of the present invention to provide a driver that can be used with sutures with pre-attached needles. It is also an object of the present invention to provide a driver which can be used without risk of an accidental needle stick.

SUMMARY OF INVENTION

The present invention is a suture anchor apparatus including an anchor which is removably insertable into a bone without requiring pre-drilling and which may be preliminarily mounted to the bone in a stable assessment position and removed from the bone with minimum damage to the bone. The apparatus also includes a driver adapted for use with the suture anchor. The invented suture anchor in its preferred embodiment includes a threaded, cylindrical portion and a forwardly extending pointed tip. The tip includes a piercing region culminating in a point and a shaft coupling the piercing region to the threaded portion. The tip may be inserted into a bone to the depth of the threads by axial motion alone. In this position, the anchor is stable and may either be screwed into an anchoring position or removed from the bone by axial motion and re-sited. The shaft has a very slight taper and is long enough to support, temporarily, the anchor and an associated driver when it is inserted into the bone.

The self-tapping threads begin just behind the shaft. The foremost flight of the threads begins with a diameter equal to that of the shaft widening to a sufficient diameter for firmly securing the anchor in the bone. Behind the threaded portion is a driving portion for coupling to the driver so that the anchor may be axially pushed into the assessment position and radially turned into the anchor position. The anchor also includes an eyelet though which the suture may be looped for securing a ligament to the bone.

The driver includes a tip with structure complementary to the driving portion of the anchor. The tip also has a passageway allowing a suture and an attached needle, which have been coupled to the anchor, to be passed through and stored in a compartment in the driver.

The invented suture anchor apparatus has the advantage of permitting the surgeon to insert the suture anchor without requiring a pre-drilled hole. This eliminates the requirement for a drill and a bit matched to the size of the suture anchor and the step of pre-drilling. The suture anchor can be held at the tip of the driver and easily positioned at the most desirable ligament-attachment point.

The invented anchor has the additional advantage of being insertable at the chosen attachment point with only an axial motion. This is less time consuming than using an anchor having a drill bit which must bore a hole starting at the surface of the bone. The axial motion is also preferable because it is better for controlling the path that the anchor will take through the cortex and into the cancellous portion of the bone. Once the anchor is inserted along its axis into the assessment position, the anchor will follow the path made in reaching the assessment position if it is screwed into an anchor position.

The invented anchor has the further advantage of being removable if the surgeon determines that another site is preferable. Because the anchor is inserted only to the depth of the threads, it leaves only a pin-hole behind when it is removed. This results in less damage to the bone structure compared with a bored hole so that the anchor may be re-sited close to the original site. The surgeon thus has the maximum freedom for siting the anchor at the surgically ideal reattachment location.

The invented anchor also has the advantage of producing a conical hole when inserted to the assessment position. If re-siting is necessary, the second hole may be placed within a diameter of the first because the threads will still gain bone purchase below the surface of the bone where the bone structure has not been impacted by the first hole.

The invented apparatus also has the advantage of providing a guard to prevent accidental sticks. The guard also functions as a handle for holding the anchor during suture installation.

The invented driver has the advantage of allowing the surgeon to pre-thread the anchor with a suture with an attached needle. The driver also has the advantage of providing a compartment to store the suture and needle attached to the anchor and permitting the installation of the anchor with the suture and needle in place without the suture becoming wrapped around the driver.

These and other objects and advantages of the invention will be more fully understood by reference to the accompanying drawings and the detailed description to follow.

BRIEF DESCRIPTION OF THE DRAWINGS

FIG. 7 is a side view of the anchor installed in the driver and held by a surgeon prior to insertion into a bone.

FIG. 8 is a side view of the anchor installed in the driver and inserted in a bone to an assessment position showing the anchor and driver standing without support except for the inserted tip of the anchor.

DETAILED DESCRIPTION OF THE PREFERRED EMBODIMENT

Figure 1:
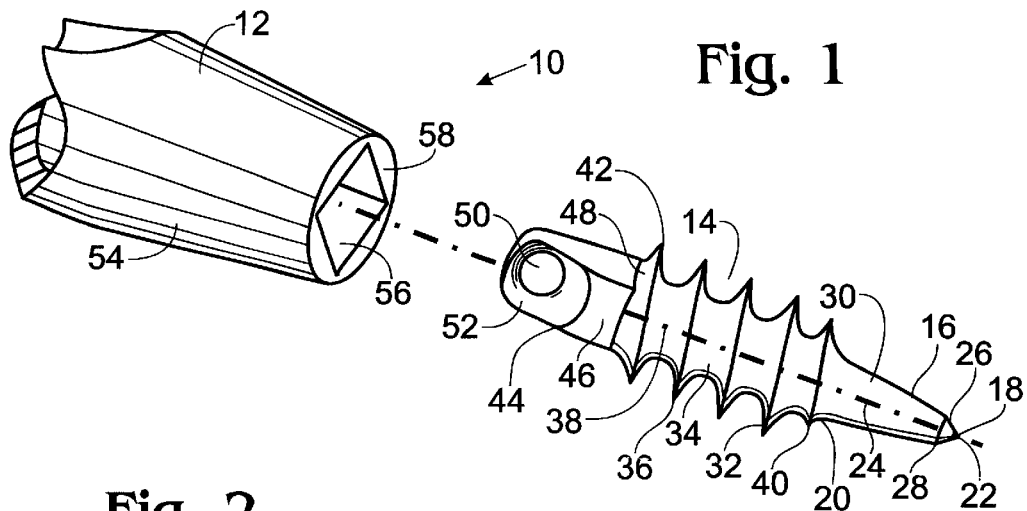
FIG. 1 is an enlarged perspective view of the invented suture anchor showing its pointed tip, conical pin, threaded portion, driving portion, suture eyelet as well as a driver which may be coupled to the driving portion of the anchor.

As shown in FIG. 1, a suture anchor apparatus according to the present invention is generally indicated at 10. The apparatus includes a driver 12 and an anchor 14. The apparatus provides a useful, removably insertable anchor which may be affixed in a bone to anchor suture to the bone. The driver is adapted to push and screw the anchor into place in the bone. The anchor is made of a bio-compatible compound, such as surgical steel, or a bio-absorbable compound.

The anchor includes an elongate tip 16 which extends from a leading end 18 back to a trailing end 20. The leading end culminates in a point 22 of sufficient sharpness to pierce the outer layer or cortex of a bone. The tip has a longitudinal axis 24 extending from the leading end to the trailing end and passing through point 22. The tip has a length measured from the leading end to the trailing end, a width measured at the trailing end, and an aspect ratio equal to the tip length divided by the tip width.

The tip of the preferred embodiment has a generally conical shape including two conical regions, a piercing region 26 extending from the point back to a boundary line 28 and a stabilizing region such as shaft 30 extending from the boundary line to the trailing end. The piercing region tapers outwardly from the point at a first taper angle, preferably about 68-degrees. The piercing region is shorter than the shaft, preferably with a length of about 0.024-inches. The shaft tapers outwardly from the piercing region at a second taper angle, preferably about 17-degrees. The shaft of the preferred embodiment is about 0.119-inches long, giving the tip an overall average taper angle of about 26-degrees over a length of about 0.143-inches. Tip width is about 0.067-inches long and the aspect ratio is about two. Shaft 30 thus has a length which comprises more than half the length of the tip and a diameter which changes along the length of the shaft by an amount less than one-half that length, giving the shaft a narrowly, or slightly tapered, conical shape that, when inserted into a bone, resists tipping out of the bone. The anchor is believed to operate as described herein with an aspect ratio as small as 1½ or an overall average taper angle of about 37-degrees. It will be understood that the tip may include more than two regions of different taper or the tip may have a single taper from the leading end to the trailing end.

Behind trailing end 20 of the tip is a threaded portion 32 including a generally cylindrical root 34 and a screw thread 36 extending outwardly from the root. The root has an elongate axis 38 collinear with axis 24 of the tip. As seen in FIG. 1, the thread begins at a first end 40 of the threaded portion which coincides with the trailing end of the tip and extends back to a second end 42 of the threaded portion. The thread increases in diameter from the tip to a maximum outside diameter of 0.15-inches over the course of the first turn. This is substantially greater than tip width. The thread has a sufficient hardness and sharpness to be self-tapping in bone and preferably the entire anchor is made out of stainless steel, titanium or other bio-compatible material.

The anchor has a driving portion 44 behind the second or trailing end of the threaded portion. The driving portion includes a polygonal structure in the form of a square post 46 for transmitting rotational motion to the threaded portion and an annular structure 48 to receive force applied along axes 24, 38. The annular structure is formed in the second end of the thread. It should be noted that a square post can transmit a greater amount of torque to the threaded portion than a hexagonal shape of the same size without stripping the corners.

A suture-securing structure in the form of an eyelet 50 is formed in post 46. The eyelet includes a beveled edge 52 to reduce wear on the suture.

FIG. 7 shows the driver having a tip 54 that narrows to a minimum diameter less than thread 36. The tip has a coupling structure 56, preferably a square opening, adapted to receive the driving portion of the anchor and an annular structure or face 58 complementary to the annular structure of the anchor.

Figure 2:
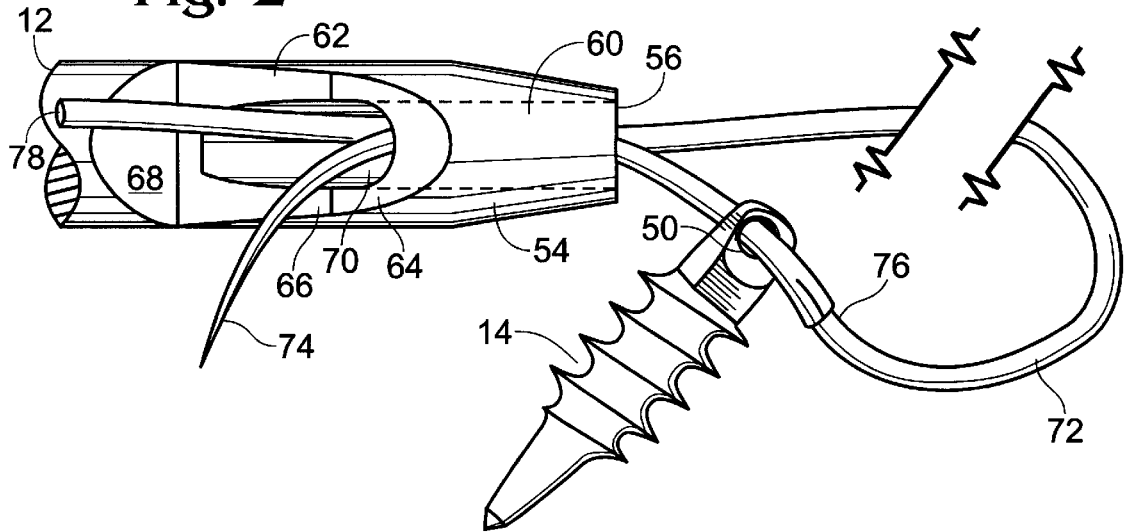
FIG. 2 is an enlarged side view of the anchor and driver showing how a suture is looped through the eyelet and passed through a passageway on the driver.

As seen in FIG. 2, driver 12 includes a passageway 60 communicating with a square opening 56. The driver also includes a cutout area 62 close to tip 54 defined by a leading wall 64, a floor 66, and a trailing wall 68. A passageway 60 communicates with a second opening 70 in leading wall 64. The anchor eyelet and the openings and passageway of the tip are sized and configured to allow a suture 72 with a pre-attached curved needle 74 to be passed therethrough. Preferably, both ends 76, 78 of the suture are passed through the driver tip.

Threading the suture through the anchor eyelet prior to installation of the anchor in a bone has two advantages. First, the suture may be used to pull the anchor into place at the tip of the driver and to hold the anchor in place. Second, the surgery is simplified by use of a pre-threaded anchor because the surgeon does not have to thread the anchor after installation. Use of a suture with a pre-attached needle is also beneficial because it eliminates the need for the surgeon to thread the needle.

Figure 3A:
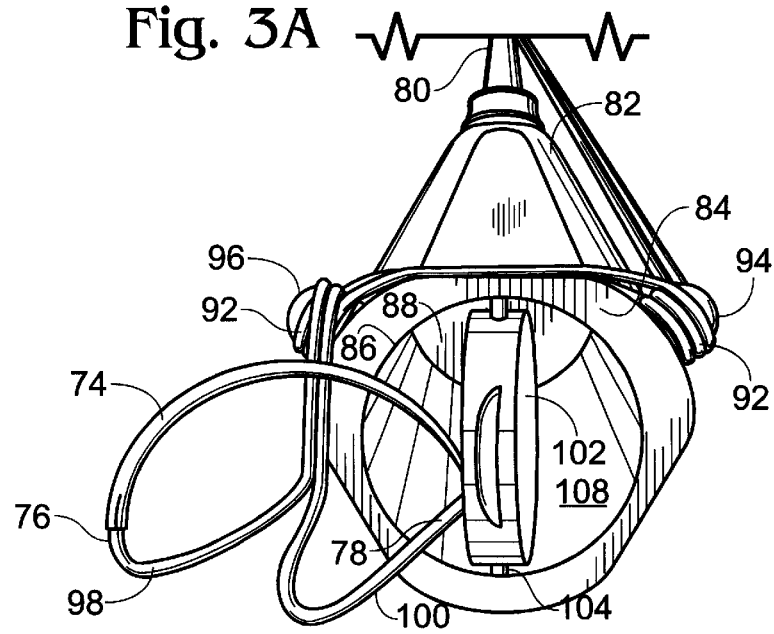
FIGS. 3A and 3B are enlarged perspective views of the driver and a storage compartment formed therein to hold a portion of the suture.
Figure 3B:
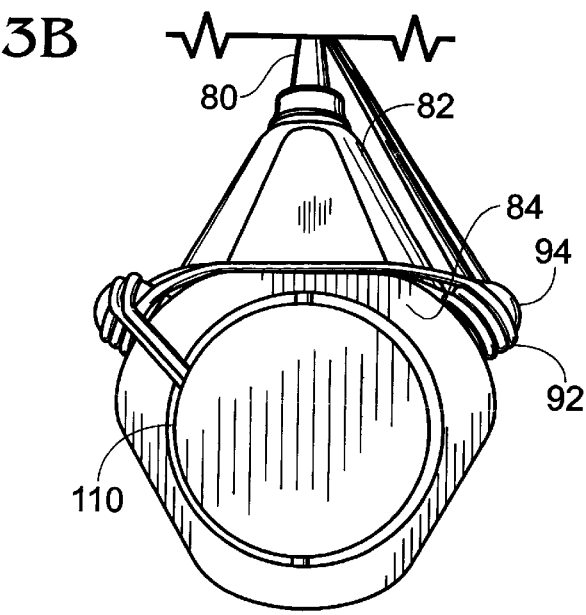

As seen in FIGS. 3A and 3B, the driver includes a shaft 80 extending back from the driver tip. A hollow handle 82 is connected to the driver shaft. At a trailing end 84, the handle has an opening 86 into a suture-storage compartment 88 in the handle. After the suture and needle are passed through the driver tip, the suture is drawn back toward end 84 and loops 92 are wrapped around a first knob 94 and a second knob 96 on handle 82. The knobs help to hold the suture in place while portions 98, 100 of the suture adjacent ends 76, 78 are inserted into compartment 88. Needle 74 and portions 98, 100 of suture 72 are inserted through opening 86 into compartment 88. A cap 102 is installed on a pivot pin 104 which extends through an inner surface 108 of compartment 88. The pivot pin is slightly off center in opening 86 causing an edge 110 of the cap to be closer to the inner surface than the opposite edge. The cap is rotatable on the pin between an open position, shown in FIG. 3A, for insertion of the suture and needle and a closed position, shown in FIG. 3B, with the suture pinched between edge 110 of the cap and inner surface 108.

Figure 4:
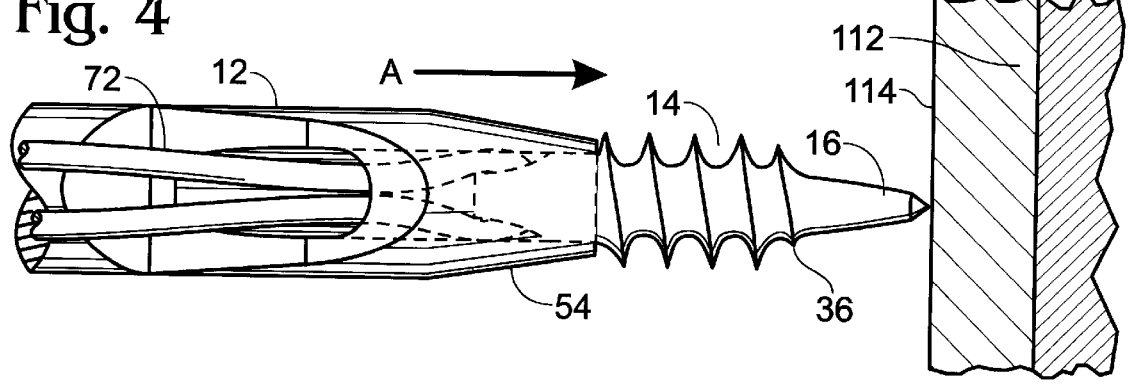
FIG. 4 is an enlarged side view of the anchor at a selected bone attachment site prior to axial insertion.
Figure 5:
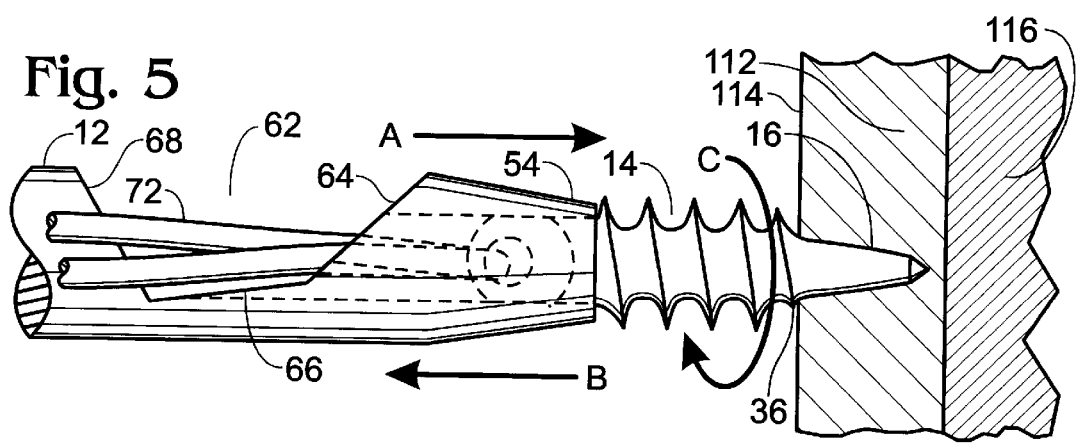
FIG. 5 is an enlarged side view of the anchor inserted by axial motion to the depth of the threaded portion.
Figure 6:
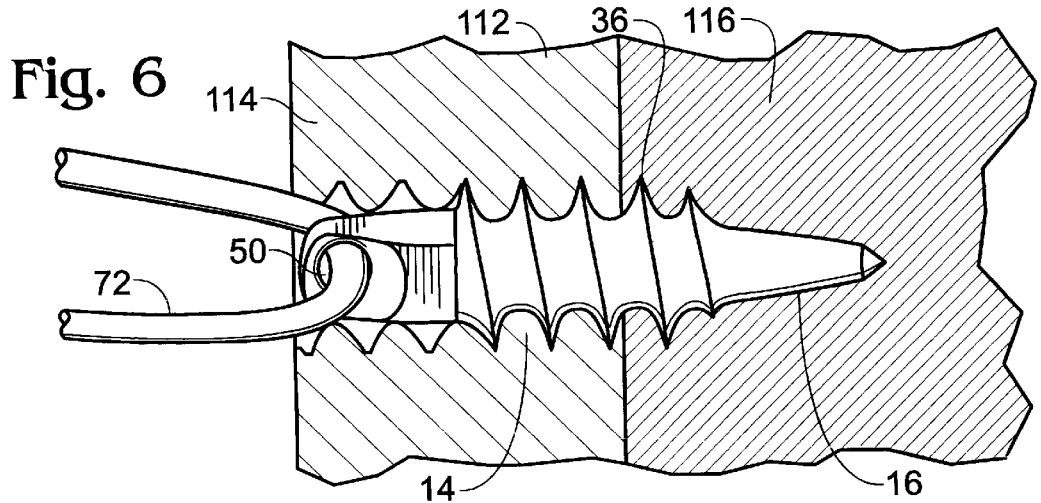
FIG. 6 is a side view of the anchor radially turned into the anchoring position with suture passing through the eyelet.

Use of the anchor is illustrated in FIGS. 4–8. Prior to insertion, the surgeon selects an appropriate site for the anchor which is then placed at the site, as seen in FIG. 4, with tip 16 touching a bone 112 at an outer surface or cortex 114. From this position, the surgeon imparts an axial motion A to the driver and anchor. FIG. 5 shows the anchor after the axial motion has pushed the anchor into an assessment position where the surgeon can determine further if this is an appropriate site for the anchor. From the assessment position, the surgeon may withdraw the anchor by reverse axial motion B or turn the anchor into place by a radially rotational motion C. FIG. 6 shows the anchor fully turned into place in an anchoring position in a cancellous portion 116 of the bone and the driver removed. The surgeon may also remove the anchor from this position, if desired, by placing the driver over the driving portion and screwing the anchor out of the bone.

FIG. 7 shows the surgeon's hand 118 holding the driver at the handle prior to insertion. The dotted lines illustrate the position the anchor will take for assessment. With the suture and needle drawn along the driver shaft and handle and stored in compartment 88, the driver may be turned to screw the anchor into place without twisting or snarling the suture. FIG. 8 illustrates that the anchor in the assessment position is stable. The anchor is stable in that the anchor will not easily come out or fall over. More particularly, the length and aspect ratio of the tip are configured such that an axial force substantially greater than the weight of the anchor is required to withdraw the anchor once the tip has been pushed in. The anchor may even be sufficiently stable to support the free-standing driver while the surgeon assesses the site, as long as the driver is positioned relatively vertically over the anchor.

Figure 9A:
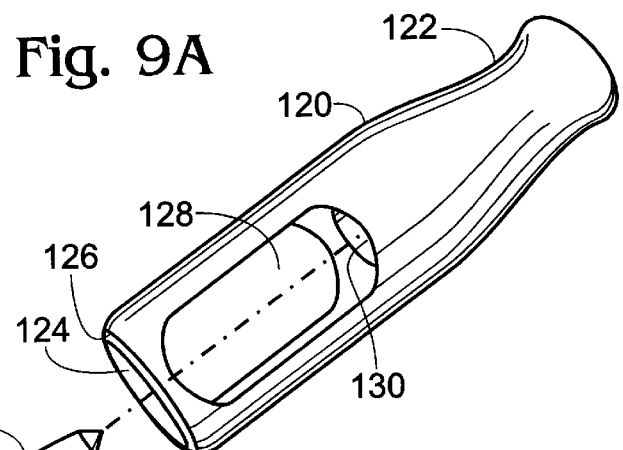
FIG. 9A is an exploded perspective view of the anchor and a guard that may be installed over the anchor tip.
Figure 9B:
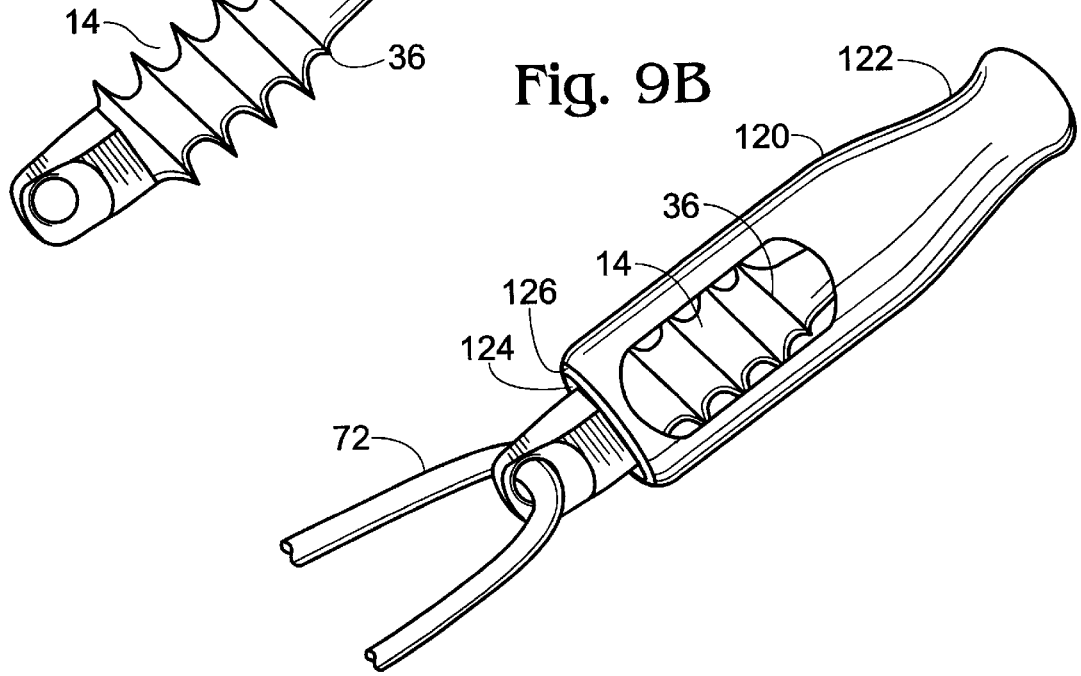
FIG. 9B is a perspective view of the anchor with the guard installed.

FIGS. 9A and 9B show a plastic guard 120 that may be attached to the anchor. The guard is used because anchors are small enough to make manipulation with gloved hands difficult. The guard includes a finger-grippable handle 122 that a surgeon or assistant may use while threading the suture into the anchor. The guard reduces the risk that the surgeon will accidentally drop the anchor while handling it with gloved hands. The guard also protects against accidental sticking by the anchor point. The guard has a generally cylindrical shape with an axial hole 124 at an end 126 opposite handle 122. The guard also has a radial slot 128 communicating with hole 124. The anchor is placed in the guard by inserting the tip into the hole and then screwing the anchor into place. A second axial hole 130 receives the tip of the anchor when the anchor is fully screwed into place.

While the present invention has been shown and described with reference to the foregoing preferred embodiment, it will be apparent to those skilled in the art that other changes in form and detail may be made therein without departing from the spirit and scope of the invention as defined in the appended claims.

I claim:

1. A suture anchor apparatus for anchoring a suture in a bone, comprising:

an anchor including an unthreaded elongate tip, a threaded portion and a suture securing structure coupled to the threaded portion, where the tip includes a leading point, a trailing end and a length along a longitudinal axis extending therebetween, the tip having an aspect ratio defined as the ratio of the length of the tip from the trailing end to the leading point along its longitudinal axis to the width of the tip at the trailing end, with the aspect ratio of the tip being greater than 1½, with the threaded portion being coupled to the trailing end of the tip and extending back therefrom and including a generally cylindrical root with a helical screw thread formed thereon, the root having an elongate axis collinear with the longitudinal axis of the tip and the threads having an outside diameter substantially greater than the width of the tip at the trailing end.

2. The suture anchor apparatus of claim 1 wherein the tip has an average taper angle of less than 37 degrees, the taper angle being the inside angle between two lines extending from the leading point to two opposing points on the perimeter of the trailing end.

3. The suture anchor apparatus of claim 1 wherein the length of the threaded portion along its longitudinal axis is no more than two times the length of the tip.

4. The suture anchor apparatus of claim 1 wherein the length of the tip is at least about 1/10 of an inch.

5. The suture anchor apparatus of claim 1 wherein the screw thread begins at the trailing end of the tip.

6. The suture anchor apparatus of claim 1 wherein the tip defines a roughly conical shape.

7. The suture anchor apparatus of claim 1 wherein the anchor further includes a driving portion coupled to the threaded portion and the apparatus further includes a driver having a tip adapted to cooperate with the driving portion of the anchor, the tip including a face for transmitting axial motion to the anchor and a coupling structure for transmitting rotational motion to the anchor, the face having a first opening leading to a passageway in the tip that terminated in a second opening, the openings and passageway being sized to allow passage therethrough of a curved surgical needle.

8. The suture anchor apparatus of claim 1 further comprising a driver having a tip adapted to cooperate with a driving portion of the anchor, the driver further having a suture-storage compartment sized to receive and store at least a portion of a the suture.

9. The suture anchor apparatus of claim 8 wherein the driver further comprises a suture-holding structure for retaining the suture in the storage compartment.

10. The suture anchor apparatus of claim 9 wherein the suture-holding structure comprises a cap for pinching the suture between the cap and an inner surface of the compartment.

11. The suture anchor apparatus of claim 9 wherein the suture-holding structure further comprises a knob disposed on the driver for receiving a loop of the suture so that the suture may be wrapped around the knob and held in place while being inserted in the compartment.

12. The suture anchor apparatus of claim 8 wherein the suture storage compartment is sized to receive and enclose a needle attached to the suture.

13. A suture anchor for insertion into a bone, the anchor comprising:
  an elongate tip with a longitudinal axis defined therethrough and having a leading point and a trailing end and a length defined therebetween, the tip having a width measured at the trailing end, the tip having a length of at least about 1/10 of an inch, the tip having an average taper between the leading point and the trailing end of less than about 37-degrees;
  a threaded portion coupled to the trailing end of the tip and extending back therefrom, the threaded portion including a generally cylindrical root and a screw thread extending outwardly from the root, the root having an elongate axis collinear with the tip axis and the threads having an outside diameter substantially greater than the width of the trailing end of the tip; and
  a suture-securing structure coupled to the threaded portion.

14. The suture anchor of claim 13 wherein the tip has a taper which is variable.

15. The suture anchor of claim 13 wherein the threaded portion includes a first annular structure so that a driver with a complementary annular structure may be used to push the anchor with axial motion into the stable assessment position.

16. The suture anchor of claim 13 further comprising a driving portion coupled to the threaded portion and wherein the driving portion includes a structure that is polygonal in cross-section so that a driver with a complementary polygonal structure may be used to screw the anchor into place.

17. The suture anchor of claim 16 wherein the polygonal structure on the driving portion is square.

18. The suture anchor of claim 13 further comprising an anchor guard having an aperture defined therein and a finger-grippable handle, the aperture being sized to removably receive the tip and threaded portion of the anchor so that the anchor may be more securely held.

19. The suture anchor of claim 13 wherein the suture-securing structure is sized to allow passage therethrough of a surgical needle.

20. A suture anchor for removable insertion into a bone, the anchor comprising:
  an unthreaded and generally conical tip having a leading end and a trailing end and a longitudinal axis defined therebetween, the tip including a cortex-piercing point at the leading point, the tip tapering from the trailing end to the leading end at an average angle of less than about 40-degrees, the tip having a width measured at the trailing end;
  a threaded portion coupled to the trailing end of the tip and extending back therefrom, the threaded portion including a generally cylindrical root having a first end coupled to the trailing end of the tip and a second end opposite the first, the threaded portion further including a screw thread extending outwardly from the root from the first end to the second end, the root having an elongate axis collinear with the tip axis and the threads having an outside diameter substantially greater than the width of the trailing end of the tip;
  a suture-securing structure coupled to the threaded portion; and
  a driving portion coupled to the threaded portion adapted to cooperate with a driver to transmit axial and rotational motion of the driver to the tip and threaded portion.

21. The suture anchor of claim 20 wherein the driving portion is a square post having an end rigidly coupled to the threaded portion.

22. The suture anchor of claim 21 wherein the suture-securing structure is an eyelet rigidly coupled to the square post at an end opposite the threaded portion.

23. The suture anchor of claim 22 wherein the eyelet is sized to permit passage therethrough of a curved surgical needle.

24. The suture anchor of claim 20 wherein the tip includes a piercing region with a first taper angle extending from the leading point of the tip back to a boundary line and a shaft with a second taper angle extending from the boundary line back to the trailing end of the tip and wherein the first taper angle is substantially greater than the second taper angle.

25. The suture anchor of claim 24 wherein the second taper angle is less than about 20-degrees.

* * * * *